(12) United States Patent
Decaluwe et al.

(10) Patent No.: US 10,757,913 B2
(45) Date of Patent: Sep. 1, 2020

(54) ANIMAL IDENTIFICATION SYSTEM INCLUDING A MALE PORTION, FEMALE PORTION AND REMOVABLE DEVICE FOR STORING A SAMPLE

(71) Applicant: Allflex Europe, Vitre (FR)

(72) Inventors: Johan Decaluwe, Laval (FR); Jean-Jacques Hilpert, Vitre (FR); Bruno Teychene, La Plaine (FR); Johan De Meulemeester, De Pinte (BE); Jean-Jacques Destoumieux, Lescure D'albigeois (FR)

(73) Assignee: Allflex Europe (FR)

( * ) Notice: Subject to any disclaimer, the term of this patent is extended or adjusted under 35 U.S.C. 154(b) by 689 days.

(21) Appl. No.: 14/801,435

(22) PCT Filed: Feb. 6, 2014

(86) PCT No.: PCT/EP2014/052348
§ 371 (c)(1),
(2) Date: Jul. 16, 2015

(87) PCT Pub. No.: WO2014/124863
PCT Pub. Date: Aug. 21, 2014

(65) Prior Publication Data
US 2016/0007567 A1 Jan. 14, 2016

(30) Foreign Application Priority Data
Feb. 12, 2013 (FR) ...................................... 13 51171

(51) Int. Cl.
*A01K 11/00* (2006.01)
*A61B 10/02* (2006.01)

(52) U.S. Cl.
CPC ........ *A01K 11/003* (2013.01); *A61B 10/0266* (2013.01); *A01K 11/004* (2013.01); *A61B 2503/40* (2013.01)

(58) Field of Classification Search
CPC .................................................... A01K 11/003
See application file for complete search history.

(56) References Cited

U.S. PATENT DOCUMENTS 3,659,587 A * 5/1972 Baldwin ............ A61B 5/15003
600/577
4,597,208 A 7/1986 Chevillot et al.
(Continued)

FOREIGN PATENT DOCUMENTS

FR 2550915 A1 3/1985
FR 2917574 A1 12/2008
(Continued)

OTHER PUBLICATIONS

International Preliminary Report on Patentability for International Application PCT/EP2014/052348, Report dated Aug. 18, 2015, dated Aug. 27, 2015, 9 Pgs.
(Continued)

*Primary Examiner* — Matthew Kremer
(74) *Attorney, Agent, or Firm* — KPPB LLP (57) ABSTRACT

The invention pertains to a system for identifying an animal comprising a male part (30), cooperating with at least one cutting element intended to cut out a sample of animal tissue, a female part (40) with open head having a through-channel, and a detachable device (50) for storing said sample, intended to be fixed to one end of said through-channel.
According to the invention, the system also comprises means for closing said head that can take at least two positions, comprising an open position enabling the passage of said sample through the through-channel during a col-
(Continued)

lecting operation, and an irreversible closed position by which the channel is closed in the vicinity of said one end (422) subsequently to the collecting operation.

8 Claims, 5 Drawing Sheets

(56) References Cited

U.S. PATENT DOCUMENTS

| | | | |
|---|---|---|---|
| 8,668,655 | B2 | 3/2014 | Destoumieux et al. |
| 2008/0034626 | A1* | 2/2008 | Brem .................. A01K 11/003 40/300 |
| 2010/0210011 | A1* | 8/2010 | Hilpert ................ A01K 11/003 435/307.1 |
| 2011/0295148 | A1* | 12/2011 | Destoumieux ....... A01K 11/003 600/564 |

FOREIGN PATENT DOCUMENTS

| | | | |
|---|---|---|---|
| FR | 2939281 A1 | 6/2010 | |
| WO | 2002039810 A2 | 5/2002 | |
| WO | WO 2010009983 A1 * | 1/2010 | ........... A01K 11/003 |
| WO | 2010066475 A1 | 6/2010 | |
| WO | 2011154510 A1 | 12/2011 | |
| WO | 2014124863 A1 | 8/2014 | |

OTHER PUBLICATIONS

International Search Report and Written Opinion for International Application No. PCT/EP2014/052348, completed Mar. 19, 2014, dated Mar. 27, 2014, 19 Pgs.

\* cited by examiner

ANIMAL IDENTIFICATION SYSTEM INCLUDING A MALE PORTION, FEMALE PORTION AND REMOVABLE DEVICE FOR STORING A SAMPLE

1. FIELD OF THE INVENTION

The field of the invention is that of the identification and/or tagging of animals.

More specifically, the invention pertains to a system for identifying animals enabling a visual and/or electronic identifying tag to be placed on any animal species and enabling a corresponding sample of tissue to be collected.

Such a collecting of tissue, which can be done simultaneously with the placing of the identification tag, makes it possible especially to preserve cells/tissues carrying the biological and/or biochemical characteristics of the animal, for example to subsequently identify the animal or detect diseases in the animal.

2. PRIOR ART

In order especially to improve the tracking of livestock, improve productivity (by eliminating diseased animals or by searching for special genetic characteristics for example), and/or guarantee the origin of the animals intended for consumption (for example by detecting diseases), it is becoming ever more frequent to carry out one or more operations for collecting of tissues from the animals concerned.

Such collecting of tissues can be done on the animal when placing an identification tag for identifying the animal (at birth for example) or later. Other tissue-collecting operations can also be carried out throughout the animal's existence, for example to detect diseases and certify the animal's identity by comparison of DNA sequences or to assess its genetic value. Once collected, the sample of animal tissue can therefore be stored and/or transmitted to a laboratory for analysis.

Thus, among currently used collecting techniques, the technique described especially in the patent application WO02/39810 filed on behalf of CAISLEY can be used to collect a sample of animal tissue simultaneously with the placing of an identification tag.

Figure 1:
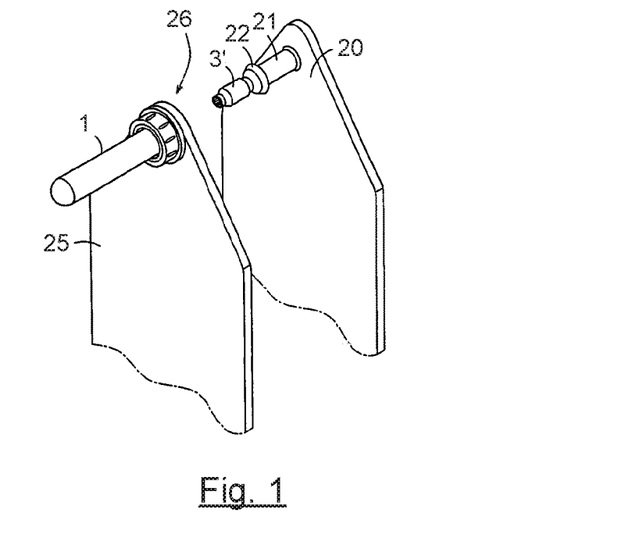
FIG. 1 presents a system for identifying animals according to the prior art.
Figure 2:
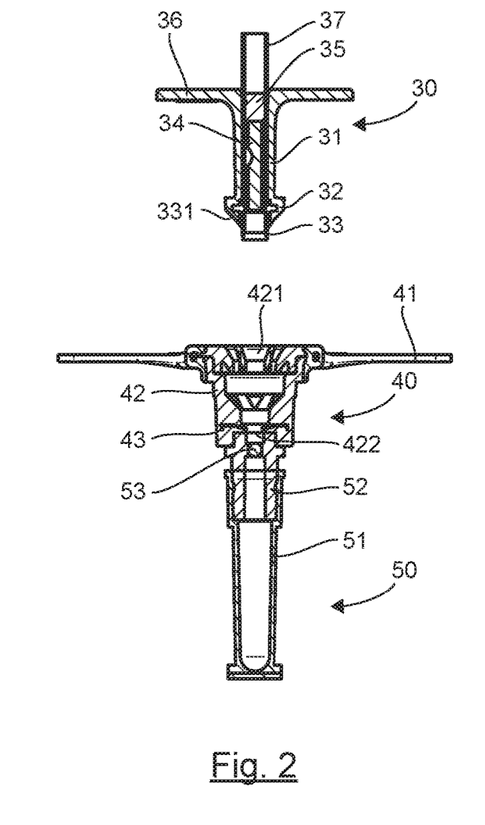
FIGS. 2 to 5 present a system for identifying animals according to one particular embodiment of the invention, at different stages of tagging/collecting.

According to this technique, illustrated in FIG. 2, a system for identifying animals comprises a male part 20, a female part 25 and a device for storing a sample 1. The male part 20 is provided with a male pin or shaft 21 having a head 22, at the end of which there is fixed a punch 3'. The female part 25 has an opening 26 for receiving the head 22 of the male part and a through-channel at the end of which there is fixed a storage device 1, prior to the collection of samples.

During the operation for collecting and placing the tag, the punch 3' cuts into the animal's ear, passes through the through-channel of the female part 25 and gets housed in the storage device 1. The storage device 1 closed by the punch 3' is then detached from the female part 25.

Such a technique offers numerous advantages since it enables the collection of animal tissue simultaneously with the placing of the tag, but also has drawbacks.

Indeed, collecting a sample simultaneously with placing an identification tag requires the use of a female part having a through-channel, also called a female part with an "open head".

Now, such a tag (or buckle) is less secure in terms of inviolability since the head of the male part remains visible and accessible after the male and female parts have been fitted together. There is therefore an increased risk that a malicious person will push the male part out of the female part, thus separating the male and female parts and replacing the tag on another animal.

There is therefore need for a novel technique that enables an identification tag to be placed simultaneously with the collecting of a sample of tissue, but does not have these drawbacks of the prior art.

3. SUMMARY OF THE INVENTION

The invention proposes a novel solution in the form of a system for identifying an animal comprising:
- a male part, cooperating with at least one cutting element intended to cut out a sample of animal tissue,
- a female part with open head having a through-channel, and
- a detachable device for storing the sample, intended to be fixed to one end of the through-channel.

According to the invention, such a system also comprises means for closing or blocking the head that can take at least two positions, comprising an open position enabling the passage of the sample through the through-channel during a collecting operation, and a definitive or irreversible closed position by which the channel is closed in the vicinity of said one end subsequently to the collecting operation.

Thus, the invention relies on a novel and inventive approach to tagging and to the collecting of animal tissues, enabling the use of an "open-head" female part for the collecting operation, and a "closed-head" female part that stays on the animal after the collecting operation.

According to the invention, the head of the female part can therefore have two states: an open state, prior to the collecting, in which the sample can pass through the head of the female part and get housed in the storage device and a closed state, subsequent to the collecting. In this way, the tag placed on the animal corresponds to a "closed head" tag considered to be more reliable than "open head" tags. In addition, if the cutting element is a punch fixed to the end of the male pin, the "closing" of the head of the female part protects the cutting edge of the punch once the tag is placed on the animal and therefore prevents cuts/injuries to the animal and/or breeders. In particular, in order to reinforce the inviolability of the tag thus obtained, the closing of the female part is irreversible.

It can be noted that the passage from the open position prior to the collecting, in which the channel is open from one side to the other to enable the passage of the sample through the through-channel during the collection, to the irreversible closed position after the collecting, in which the channel is closed in the vicinity of its end at which the detachable storage device was fixed, can be commanded by the collecting operation. For example, the closing means can be commanded by the withdrawal of the detachable storage device and/or the moving of a part in the system, such as for example the sliding of the plug of the male part in the female part and/or a positioning and collecting tool According to a first embodiment, the means for closing comprise a plug.

Such a plug can be inserted by hand into the through-channel of the female part in the vicinity of the end to which the storage device was fixed, or it can be done automatically or almost automatically, i.e. without any particular action on the part of the user after the collecting operation.

In particular, the closing means comprise means for retaining the plug in the closed position.

These means for retaining, which are localized within the female part and fixedly attached to the female part, are not visible or accessible. They therefore maintain the plug in a sure and definitive manner.

According to a first example, the retaining means comprise a washer having at least one spring leaf or claw.

It is for example a "Starlock" (registered mark) type of stop washer.

According to a second example, the retaining means comprise at least one bolt which can take at least two positions, of which one is an unlocked position in which the bolt or bolts are held in position by the storage device and one is a locked position in which the bolt or bolts are released and retain the plug.

In particular, the locked position is obtained when the storage device is detached from the female part. Thus, if a malicious person tries to replace the initial storage device by another one (having another identification number for example), the head gets closed when the initial storage device is detached from the female part and it is no longer possible to fix another storage device thereto. It is therefore impossible to exchange the storage devices of the sample.

According to one particular aspect of the second exemplary embodiment, the retaining means also include at least one blocking element (of a bead, ball, or cylinder type for example) enabling the bolt or bolts to be blocked in the locked position.

According to a third example, the retaining means comprise a spring-forming part comprising at least two mobile jaws such that, in said open position, said jaws are stressed in opening and hold said storage device and, in said closed position, said jaws are released and lock said plug.

According to this third example, the passage from the open position to the closed position can be activated by the withdrawal of the storage device According to one particular characteristic of these examples of embodiments, the plug comprises at least one groove intended to receive an unattached end of the spring leaf or spring leaves, or of the bolt or bolts, or of the jaw or jaws in the closed position.

According to a fourth example, the plug has a first diameter in the open position and a second diameter, greater than the first diameter, in the closed position.

Such a plug which has a shape (cylindrical or spherical) generated by revolution can therefore be expansive and increase in volume when it is in the vicinity of the end of the female part to be plugged.

According to a fifth example, the plug comprises a specific substance released in the closed position.

Such a specific substance enables for example a chemical reaction between said substance and the material of the female part (or of an element of the female part) such as a reaction of polymerization enabling the plug to be "soldered" to the interior of the female part. In particular, it can be a glue or a resin.

In particular, the plug can be present in a pin of the male part in the open position.

Thus, the plug is planned in the male part and can get inserted automatically or almost automatically into the means for retaining the female part after the collecting.

According to a second embodiment, the means for closing comprise at least one shutter that is mobile between two positions, including the open or unlocked position in which the shutter or shutters are held in position by the storage device and the closed position in which the shutter or shutters shut off the channel in the vicinity of the end to which the storage device was fixed.

According to this second embodiment, the passage from the open position to the closed position can be activated by the withdrawal of the storage device. In other words, the shutter or shutters are released when the storage device is detached/withdrawn from the female part Thus, rather than introduce a plug inside the through-channel passing of the female part, one or more shutters can be provided to block the end of the channel to which the storage device can be fixed. These closing means are fixedly attached to the female part.

For example these shutters can take the form of flaps or jaws.

Thus, the closing means comprise for example a spring-forming part comprising at least two mobile jaws such that, in the open position, said jaws are stressed in opening and hold said storage device and, in said closed position, said jaws are released and shut off the channel in the vicinity of the end to which the storage device is fixed.

According to another particular characteristic, the system for identifying animals comprises a reinforcement element inserted into the pin of the male part, also called a stiffener, intended to reinforce the rigidity of the pin during the collecting operation.

Thus, rather than use a rigid male pin which has the risk of breaking if the identification tag of the animal gets wedged in an obstacle (an enclosure, a barrier, a branch, etc) which would lead to the loss of the tag, it is possible to use a "flexible" material of the polyurethane type for example that is deformable enabling especially the animal to free itself from such an obstacle.

Such a reinforcement element is, for example, a detachable reinforcement tube inserted into the male pin to reinforce the rigidity of the pin during the collecting/tagging operation. Once the tag has been placed, the reinforcement tube is withdrawn from the male pin which can get deformed.

According to one variant, the reinforcement element is a spring with contiguous turns. Such a spring enables the transmission of a force to the cutting element during the collecting/tagging operation. Furthermore, it has compression strength, and this prevents the male pin from getting compressed. Once the tag has been placed, a spring of this kind enables the bending/deformation of the male pin, especially when the male pin is made out of a "flexible" material.

Such a reinforcement element also serves as a guide for the plug when it is present in the male part in the open position.

According to another aspect of the invention, the male part, the female part and the collecting device each carry an identifier enabling the animal to be identified.

These three elements can carry the same identification number of the animal, or they can have identifiers that are related to one another. In every case, these identifiers are used to encode the same piece of information, i.e. to identify the same animal.

In this way, it is ensured that the animal and the sample collected are accurately identified and linked.

Yet another aspect of the invention pertains to a system for identifying also comprising a pusher element that is mobile relative to the cutting element, enabling the sample to be pushed into the storage device and the storage device to be shuttered or closed off.

According to this aspect, the invention enables an optimized collecting that is especially simple and fast for the user. The use of two distinct elements, one to cut out the tissues and the other to push the sample has many advantages. For example, cutting out the tissues and then pushing the sample into the storage device ensures efficient cutting out of the sample and prevents hairs from staying wedged between the walls and the plug of the storage device. These two distinct elements also provide for better collecting. Indeed, since the cutting element is not intended for insertion into the storage device, it is possible to increase the size of the cutting element, i.e. the length of its cutting edge and therefore to increase the size of the collected sample. In addition, a potential contamination of the sample is prevented since the user does not have to act directly on the sample. Besides, since the sample is cut out by the cutting element and then automatically pushed into the storage device by a pusher element, no portion of the tool or no external element is in direct contact with the collected tissue.

In particular, the storage device comprises a tube and a tube head, the tube head forming a support configured to serve as a supporting surface for the cutting element to cut out the sample and comprising an aperture enabling the insertion of at least one portion of the pusher element into the storage device.

The use of a tube head provides many advantages. First of all, it can provide a support on which the cutting element can rest to properly cut out the tissues from the animal. It also enables the closure of the tube, for example by fitting or clipping the pusher element into the tube head. In addition, the presence of such a tube head enables the opening of the tubes by the test laboratory to be automated. The opening is done by decapsulating the tube head so that only the sample remains inside the tube.

In particular, prior to the collection, the tube is closed by a spherical or cylindrical type of weighted element.

Thus, in a first position, the weighted element is held in the upper part of the storage device and blocks an inlet hole of the tube. In this first position prior to the collecting operation, corresponding for example to the form in which the tubes are commercially distributed, the weighted element fulfills the function of a plug for the tube thus preventing the insertion of impurities into the tube and therefore the contamination of the interior of the tube by the external environment.

In the second position after the collecting operation, the weighted element is released in the tube. It can then fulfill the function of a stirrer or mixer. It can also act as ballast, enabling the sample to be made to sink to the bottom of the tube, or as a "pestle", or again as a visual indicator of a successful collecting operation.

4. LIST OF FIGURES

Other features and advantages of the invention shall appear more clearly from the following description of one particular embodiment given by way of a simple illustratory and non-exhaustive example and from the appended drawings, of which.

5. DESCRIPTION OF ONE EMBODIMENT OF THE INVENTION

The invention pertains to a system for identifying animals that can be used to collect animal tissue and, at the same time, to place an identification tag, and that reinforces the inviolability of the tag that is placed.

To this end, the general principle of the invention relies on the use of a female part that can take two states, one "open head" state prior to the collecting operation and one "closed head" state after the collecting operation.

More specifically, a system for identifying animals according to the invention comprises:

a male part cooperating with at least one cutting element that is intended to cut out a sample of animal tissue;

a female part with an open head having a through-channel, i.e. a channel open from one side to the other side, and a detachable device for storing samples, that is intended to be fixed to one end of the through-channel.

The system also comprises means for closing the head capable of taking at least two positions, comprising an open position enabling the passage of the sample through the channel during a collecting operation and a closed position enabling the channel to be closed in the vicinity of the end at which the storage device was fixed, after the collecting operation.

Here below, a description is provided of a first embodiment of the invention in which the means for closing the head of the female part include a plug.

More specifically, as illustrated in FIG. 2, we consider a system for identifying animals comprising a male part 30, a female part 40 and a storage device 50.

The male part 30 is provided with a male pin 31 that extends from a base 36 and can serve as a tagging support. This base can take the form of a disk, a square, a rectangle, a label, etc. The male pin has a head 32 at its end shaped like a truncated cone tip. A cutting element 33, also called a punch, is fixed to the end of the truncated tip 32 and has a cutting edge enabling the animal's tissues to be cut out. As the case may be, the cutting element comprises a support 331 (for example made of rigid plastic), over-molded during the manufacture of the male part, so that the cutting element is fixedly joined to the male pin. According to another alternative embodiment, the cutting element takes a form of a biopsy needle which slides within the male pin to cut out the animal's tissues.

A cutting element 33 is open at both its ends in order to let through, firstly, the pusher element 34 by which the cut-out tissue sample cut can be pushed into the storage device and, secondly a plug 35 by which the head of the female part can be closed.

The pusher element 34 and the plug 35 are therefore mobile relative to the cutting element 33 and can slide through the cutting element 33 to:

push the tissue sample and close the storage device 50 for the pusher element 34, and push the pusher element 34 and close the head 42 of the female part for the plug 35.

The pusher element 34 and the plug 35 advantageously have a shape generated by revolution and a diameter slightly smaller than that of the cutting element in order to be able to slide within the cylinder forming the cutting element.

It can be noted that the use of a pusher element is described especially in the patent application WO2010/066475 filed on behalf of the same Applicant and shall not be described in further detail.

Naturally, the use of such a pusher element is optional and corresponds solely to a particular embodiment of the invention.

Finally, a reinforcement element 37, also called a stiffener, can be inserted into the pin 31 of the male part to reinforce the rigidity of the male pin during the tagging and/or collection, especially when the male part is made out of a flexible plastic material such as polyurethane. Such a reinforcement element is, for example, a detachable reinforcement tube inserted into the male pin preliminarily to the collecting operation and/or fixedly attached to the collecting tool and then withdrawn after the collecting operation. Advantageously, it remains fixedly joined to the collecting tool after the collecting and can be ejected from the tool in a classic manner (by pressing a trigger for example). According to one variant, the reinforcement element is a spring with contiguous turns that has compressive strength, thus preventing the male pin from getting compressed. Once the tag has been placed, such a spring enables the bending/deformation of the male pin.

Such a stiffener takes for example the shape of a hollow cylinder open at both its ends, inside which there slides the pusher element 34 and the plug 35. It can extend throughout the length of the male pin, starting from the base of the cutting element (non-cutting end). It can thus transmit a force to the cutting element during the tagging and collecting operations. In addition, the positioning of a stiffener enables the use of a short-length cutting element.

The female part 40 for its part comprises a base 41 which can serve as a writting support. As in the case of the male part, this base can take different forms (disk, square, rectangle, label, etc).

Besides, in the initial state, the female part 40 also has an open head 42. Such a head 42 comprises a through-channel, namely a channel open from one side to the other, making it possible to at least partially receive the pin 31 of the male part, introduced by a first end 421 of the channel. A storage device 50 can be fixed to the other end 422 of the channel.

According to this first embodiment, the female part 40 also comprises retaining means 43 used to retain the plug 35 in the female part in the closed position so as to close the channel in the vicinity of the end 422 to which the storage device 50 can be fixed.

Finally, the storage device 50, according to this first embodiment, comprises a tube 51 intended to receive the sample, provided with a tube head 52 and a weighted element 53, for example a bead or a ball.

A storage device of this kind can be fixed by any means to the end 422 of the head of the female part. For example, such a device can be screwed into the through-channel of the female part, force-fitted into the female part, clipped to the female part, etc.

According to this example, the tube head 52 is fixedly attached to the inlet of the tube 51, for example by being clipped on, fitted in, etc. It can be made flexibly, especially out of rubber, to facilitate its insertion into the neck of the tube. More specifically, the tube head 52 takes the form of a hood pierced with a central aperture, having a diameter sufficient to enable the insertion of the bead 53. The tube head 52 also has a flange capable of taking support on a rim of the tube 51. The use of such a flange makes it possible especially to facilitate the positioning and removal of the hood. The flange also defines a stop surface on which the cutting edge of a cutting element can take support during the collecting operation in order to cut out the tissue sample more easily.

Thus, in a first position prior to the collecting of the sample, the bead 53 is held in position in the storage device and shuts the inlet hole of the tube 51 to ensure a plug function for the tube. In a second position, subsequent to the collecting of the sample, the bead is introduced into the tube at the same time as the sample and is released inside the tube. It can therefore fulfill a stirrer or mixer function, or a function of ballast, a pestle or again a visual indicator of a successful collecting operation.

Naturally, the use of a tube head and/or a bead-type weighted element is optional and corresponds solely to a particular embodiment of the invention.

Finally, the shape of the receiving tube 51 is considered to be compatible with a rack-type support of sample tubes comprising for example 24, 48 or 96 positions.

According to the invention, as illustrated in FIG. 2, the female part 40 has an open head (i.e. a through-channel) prior to the tagging and collecting operations. The male part 30 and female part 40 and the storage device 50 in this initial state can be mounted on a placing tool.

For the sake of simplification, the placing tool is not shown in the figures. It is a tool that works in two stages, enabling the simultaneous shifting of the cutting element and the plug (and possibly the pusher element which, it may be recalled, is optional) in a first stage and then the shifting of only the plug (and possibly the pusher element) in a second stage. Such a tool is especially described in the patent application WO2011154510 filed on behalf of the present Applicant.

Figure 3:
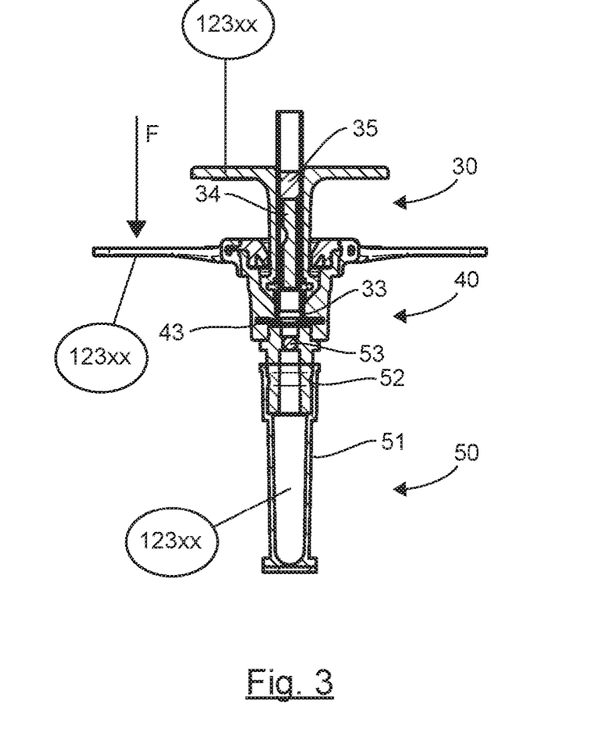

As illustrated in FIG. 3, during this operation of tagging and collecting, the male and female parts are fitted together. More specifically, a first motion of translation brings the cutting element 33 into contact with the tissues of the animal, cuts the tissues out and at least partially introduces the pin 31 of the male part into the through-channel of the female part.

Figure 4:
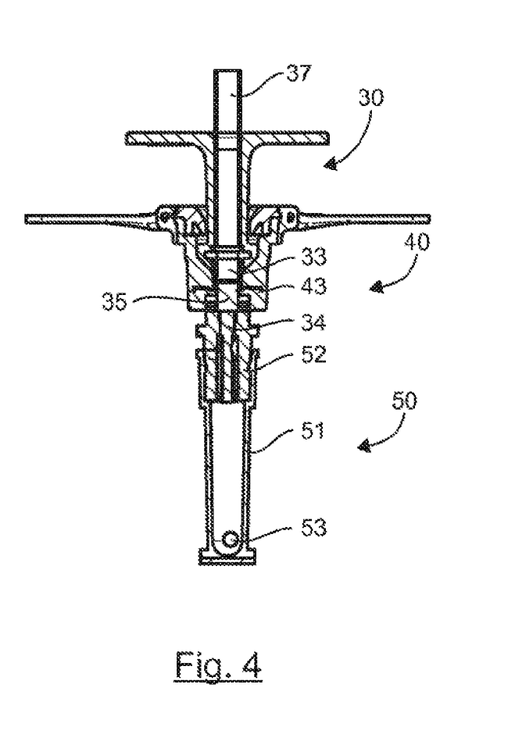

When the cutting element 33 comes to a stop against a tube head 52 (possibly by means of the retaining means 43), a second motion of translation, along the same axis of translation as the first motion, is activated enabling the pusher element 34 and the plug 35 to be pushed through the cutting element 33 along the direction illustrated by the arrow F, as illustrated in FIG. 4.

More specifically, the pusher element 34 slides through the cutting element 33, pushes the sample of tissues and the bead 53 into the tube 51 and gets fitted into the tube head 52, thus hermetically or almost-hermetically shutting off the tube 51.

Similarly, the plug 35 pushes the cutting element 34, slides through the cutting element 33 and stops its travel when it is retained by the retaining means 43, thus shutting off the end 422 of the through-channel of the head 42 of the female part.

The collecting and tagging operations are then performed.

Figure 5:
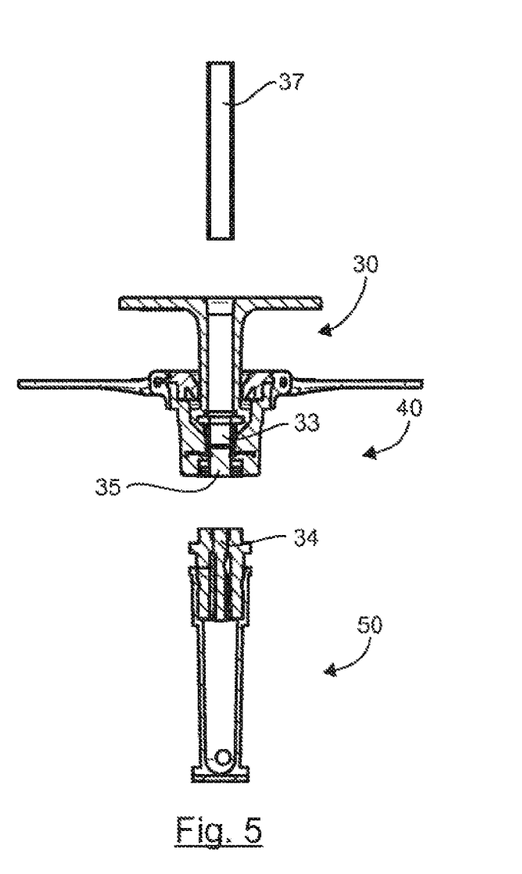

As illustrated in FIG. 5, the identification tag formed by the fitting together of the male part 30 and the female part 40 remains on the animal (in its ear for example) and the reinforcement element 37 and the storage tube 50 containing the collected sample remain held by the positioning tool. They can be ejected or withdrawn in a conventional way.

Here below, a detailed description is given of the means for closing the head of the female part according to this first embodiment implementing a plug 35.

According to a first example, the retaining means 43, present in the female part are considered to comprise a washer having at least one leaf spring or claw. This is for example a Starlock type stop-washer (registered mark)

which can be over-molded inside the head of the female part or assembled with the head of the female part.

Such a washer is positioned in the vicinity of the end 422 of the channel with which the storage device can be fixed. The main axis of the washer and that of the channel of the female part coincide. The washer therefore does not prevent the passage of the tissue sample and of the pusher element 34. However, the washer retains the plug 35.

For example, the plug 35 comprises one or more grooves within which are inserted the spring leaf or spring leaves to retain the plug 35. In this way, the plug 35 is blocked in the vicinity of the end 422 of the channel to which the storage device can be fixed and the head of the female part is in a closed state. These retaining means hold the plug securely and irreversibly.

Figure 6:
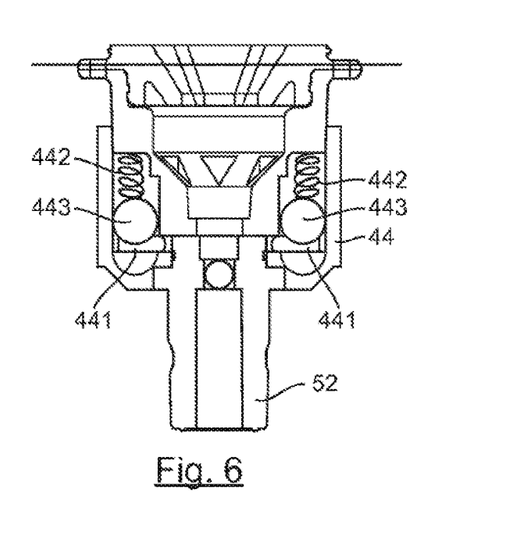
FIGS. 6, 7, 10 to 12 illustrate an example of implementation of the means for retaining a plug according to a first embodiment of the invention.
Figure 7:
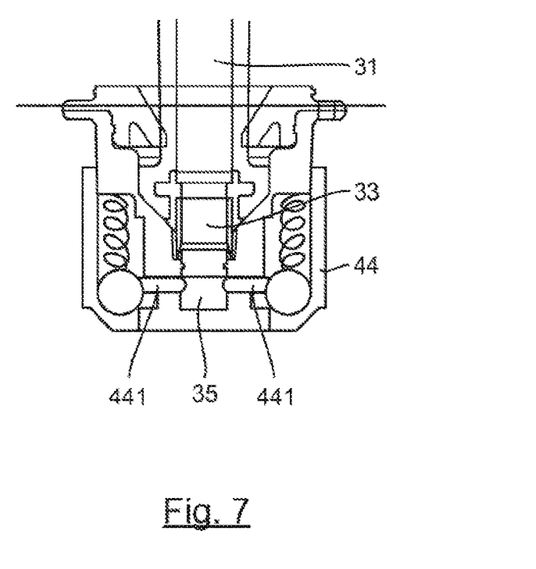

According to a second example illustrated in FIGS. 6 and 7, the retaining means include one or more bolts 441 (for example three of them) which can take at least two positions, an unlocked position illustrated in FIG. 6 in which the bolt or bolts 441 are held in position by the storage device and a locked position illustrated in FIG. 7 in which the bolt or bolts 441 are released and retain the plug 35.

More specifically, the female part 40, in the second example, comprises a cap 44 partially covering the head 42 of the female part and the storage device 50 in the vicinity of the end 422 of the channel to which the storage device can be fixed.

Prior to the collecting operation, and during the collecting operation, the storage device 50 is fixed to the female part 40. For example, the tube head 52 is fitted into the cap 44. The bolt or bolts 441 are held in an unlocked position by the tube head 52. A force is also exerted on the bolt or bolts 441 by means of one or more return elements 442 of a compression spring type for example, and one or more blocking elements 443 (for example three of them) of a bead type for example, in order to hold them in position.

Subsequently to the collecting operation, the storage device 50 is detached from the female part 40. The bolt or the bolts are then released and slide along the head 42 in the vicinity of the end 422 of the through-channel to which the tube head 52 was previously fixed, so as to grip the plug 35 in the locked position. For example, if the plug 35 has at least one recess or groove, the bolt or bolts slide to get engaged in the groove or grooves so as to retain the plug 35 in the vicinity of the end 422.

The sliding of the bolts 441 releases a space for the blocking elements 443. Under the effect of the return elements 442, which expand, the blocking elements 443 are pushed into this housing and thus block one or more bolts into the locked position. In this way, the plug 35 is blocked in the vicinity of the end 422 of the channel to which the storage device can be fixed and the head of the female part is in a closed state.

As above, these retaining means are used to hold the plug 35 securely and irreversibly.

Figure 10:
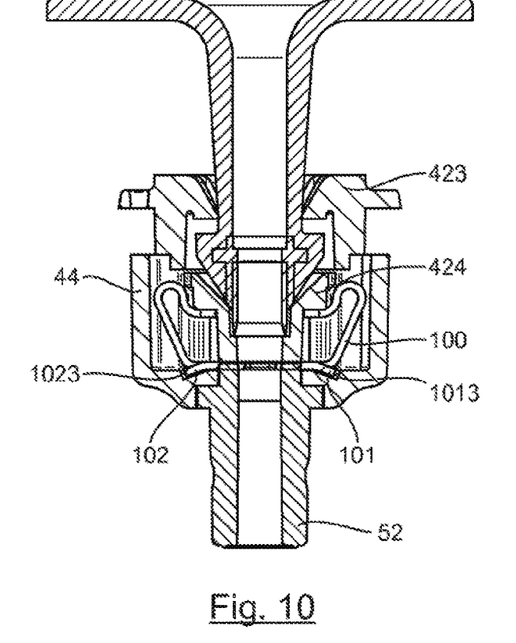
Figure 11:
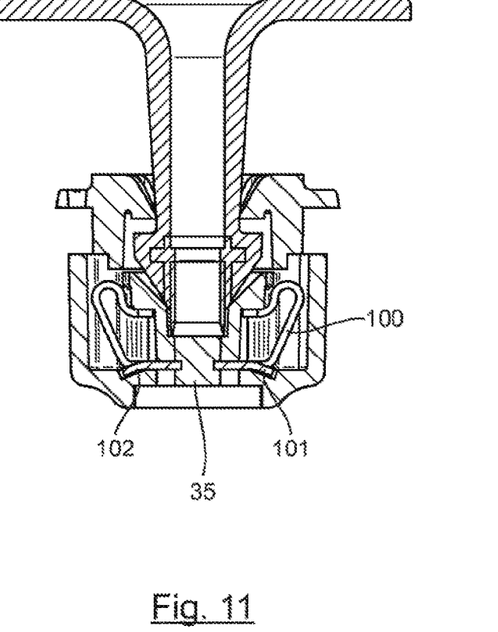
Figure 12:
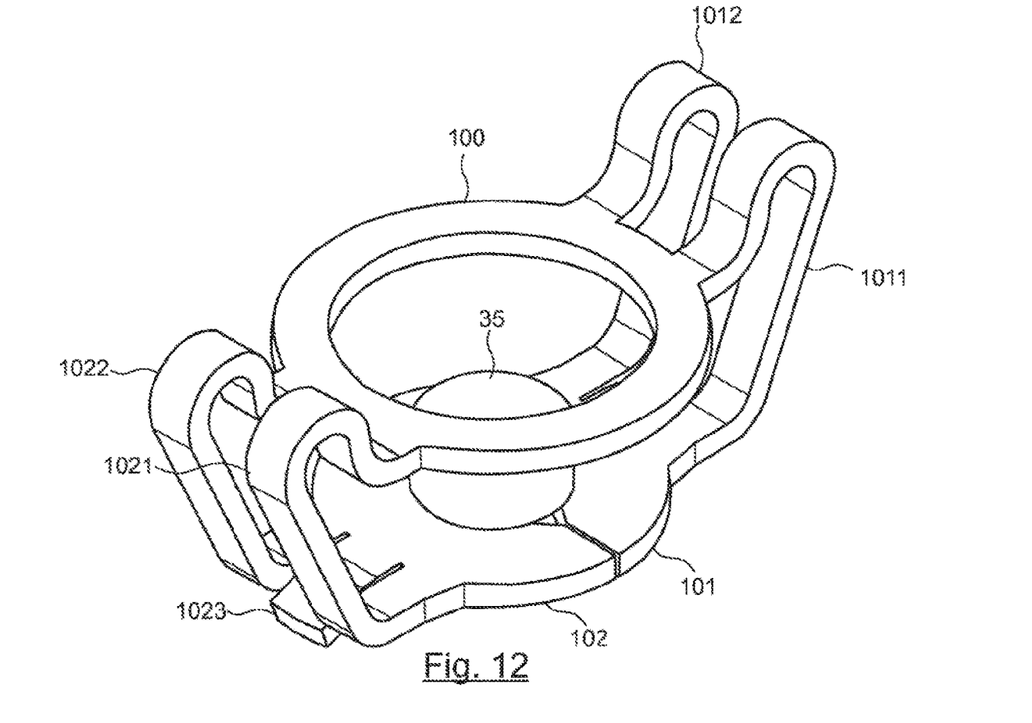

According to a third example illustrated in FIGS. 10 to 12, the retaining means comprise a spring-forming part 100 comprising at least two mobile jaws 101, 102 such that in the open position, illustrated in FIG. 10, said jaws 101 and 102 are stressed in opening and keep the storage device at the tube head 52, and such that in the closed position, illustrated in FIG. 11, the jaws 101 and 102 are released and lock the plug 35.

It can be noted that the passage from the open position to the closed position can be activated by the withdrawal of the storage device.

To this end, each of the jaws can be associated with at least one spring leaf tending to close the two jaws 101 and 102. For example, the jaw 101 is connected to two spring leaves 1011 and 1012 enabling it to be moved away in the open position and to be drawn back in the closed position. The jaw 102 for its part is connected to two spring leaves 1021 and 1022 enabling it to be moved away in the open position and to be drawn back in the closed position.

In this third example, the female part also comprises a cap 44 partially overlapping the head of the female part, and the storage device, in the vicinity of the end of the channel to which the storage device can be fixed. It can be noted that in this embodiment, the head of the female part is formed by a ring 423 enabling the head of the male part to be retained in the female part and a centering element 424 which can be used to ensure an accurate positioning of the head of the male part and the female part, in order to perform the collecting.

Prior to the collecting, and during the collecting, the storage device is fixed to the female part. For example, the tube head 52 is held in the cap 44 by the jaws 101 and 102 which grip it. It can be recalled that, in this first opening position, the jaws are stressed in opening.

After the collecting, the storage device is detached from the female part. The stress applied to the jaws 101 and 102 is released and the jaws get closed in the vicinity of the end of the through-channel to which the tube head 52 was previously fixed to grip the plug 35 in the closed position. For example, the plug 35 has at least one groove or ridge, the jaws can engage in the groove or grooves so as to retain the plug 35 in the vicinity of the end 422.

According to one advantageous variant, tabs 1013 and 1023 are respectively planned between the two leaf springs 1011 and 1012 connected to the jaw 101 and between the two spring leaves 1021 and 1022 connected to the jaw 102. Such tabs 1013 and 1023 especially prevent the return of the jaws 101 and 102 to the open positions, thus securing the locking of the plug 35.

Besides, in another advantageous variant, the two jaws 101 and 102 have a shape adapted to cooperating with the tube head 52 in the open position and to cooperating with the plug 35 in the closed position.

As here above, these retaining means enable the plug 35 to be held securely and irreversibly.

According to a fourth example which is not shown, the means for closing comprise a plug having a first diameter in the open position and a second diameter greater than the first diameter in the closed position.

A plug of this kind can be expansive and can increase in volume when it is in the vicinity of the end of the female part to be plugged. For example, the plug has an alveolate structure which is compressed in the open position, when the plug is present in the male pin for example. When the plug penetrates the channel of the female part, which has a diameter wider than the internal diameter of the male pin, the alveolate structure can resume its original shape and thus shut off the channel.

According to a fifth example, not shown, the plug comprises a specific substance, released in the closed position.

Such a specific substance enables for example a reaction with the material of the channel of the female part such as a polymerization so as to enable the plug to be "soldered"/welded within the female part. In particular, such a specific substance can be a glue or a resin.

It can be released by perforation of the plug. To this end, a perforator element can be provided in the through-channel of the female part.

Figure 8:
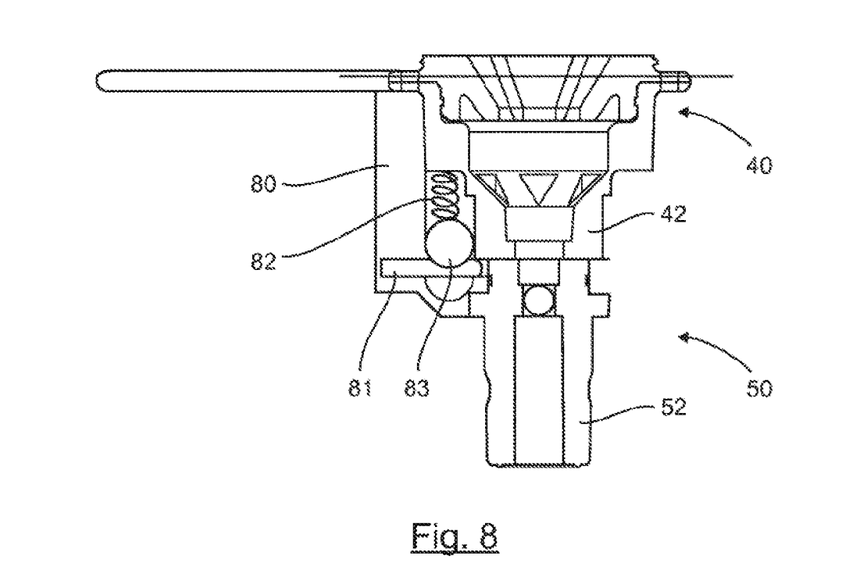
FIGS. 8, 9, 13 and 14 illustrate an example of implementation of the means for closing according to a second embodiment of the invention.
Figure 9:
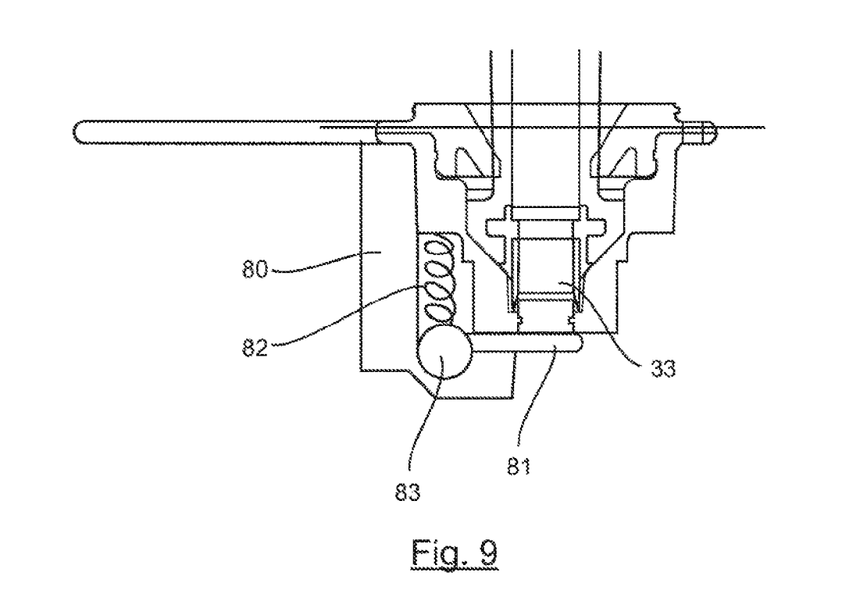

FIGS. 8 and 9 illustrate a second embodiment of the invention in which the means for closing comprise at least one shutter 81 that is mobile between two positions, including the open or unlocked position, illustrated in FIG. 8, in which the shutter is kept in position by the storage device and the closed or locked position, illustrated in FIG. 9, in which the shutter is released when the storage device is detached from the female part, and shuts off the channel in the vicinity of the end to which the storage device was fixed.

More specifically, the female part 40, in this second embodiment, comprises a cap 80 partially covering the head 42 of the female part and the storage device 50.

Prior to the collecting and during the collecting, the storage device 50 is fixed to the female part 40. The shutter or flap 81 is held in an open or unlocked position by the tube head 52. A force is also exerted on the shutter 81 by means of one or more return elements 82, of a compression spring type for example, and one more blocking elements 83, of a bead type for example, to hold it in position.

Subsequently to the collecting, the storage device 50 is detached from the female part 40. The shutter slides along the head 42 in the vicinity of the end 422 of the through-channel to which the tube head 52 was previously fixed to shut off the end 422 of the channel in the closed or locked position.

The sliding of the shutter 81 releases a space for the blocking element 83. Under the effect of the return element 82 which expands, the blocking element 83 is pushed into this housing and thus blocks the shutter 81 in the locked position. In this way, the shutter closes the end 422 of the channel securely and irreversibly, and the head of the female part is in a closed state.

Figure 13:
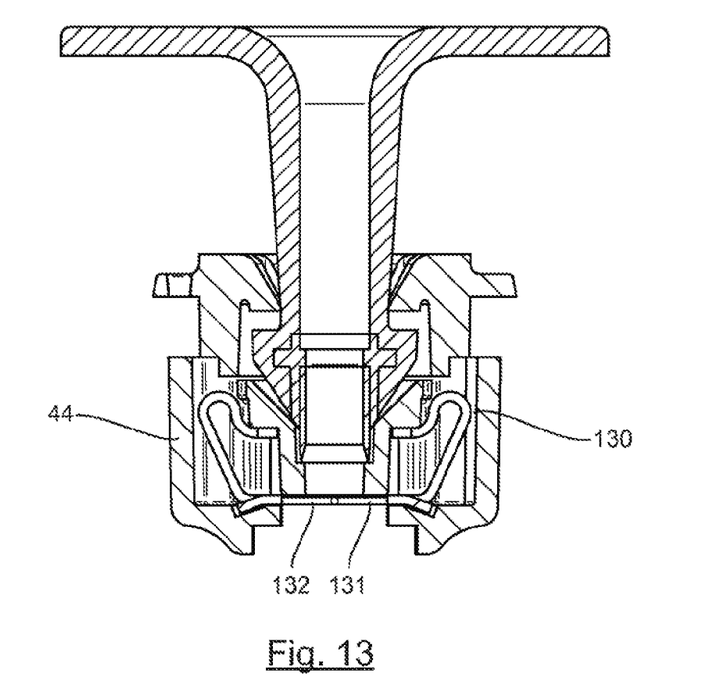
Figure 14:
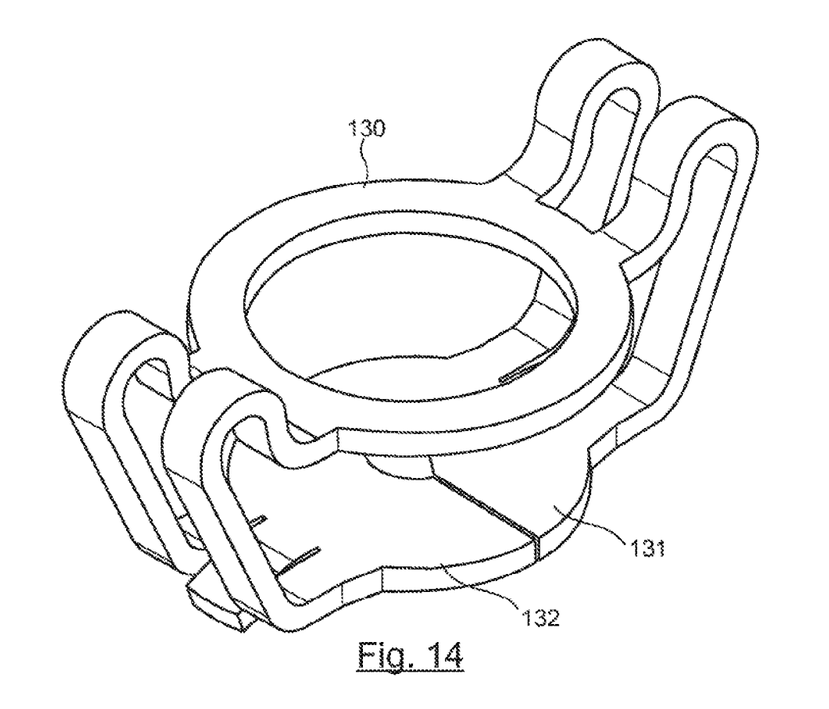

FIGS. 13 and 14 illustrate another example of this second embodiment of the invention in which the closing means comprise a spring-forming part 130 comprising two mobile shutters called jaws 131 and 132 such that in the open position (not shown but similar to the position illustrated in FIG. 10), the jaws 131 and 132 are stressed in opening and maintain the storage device at the level of the tube head and, in the closing position illustrated in FIG. 13, the jaws 131 and 132 are released and shut off (at least partially) the channel in the vicinity of the end at which the storage device is fixed.

The spring-forming part 130 is similar to the part 100 described with reference to FIGS. 10 to 12. Its working is therefore identical and is not repeated in detail. It can be noted only that, according to this second embodiment, the two jaws 131 and 132 advantageously have a shape adapted to cooperating with the tube head 52 in the open position and to closing the channel in the vicinity of the end at which the storage device was fixed in the closed position.

In the same way, the female part also has, in this example, a cap 44 as described with reference to FIGS. 10 to 12.

Prior to the collecting and during the collecting, the storage device is fixed to the female part. For example, the tube head is maintained in the cap 44 by jaws 131 and 132 which grip it. It can be recalled in this first open position, the jaws are stressed in opening.

After the collecting, the storage device is detached from the female part. The stress applied to the jaws 131 and 132 is released and the jaws get closed in the vicinity of the end of the through-channel at which the tube head was previously fixed.

Other embodiments can of course be envisaged, implementing a plug, a shutter or another element to close the head of the female part.

In particular, although the embodiments described with reference to FIGS. 2 to 5 provide for the presence of a pusher element and of a reinforcement element, it may be recalled that these elements are optional. The working of the invention, i.e. the closing of the head, is similar whether or not the system for identifying animals uses these elements. In particular, if a reinforcement element is not used, it is possible to use a male pin made out of hard material or to use a plunger of the positioning tool or a biopsy needle to rigidify the male pin. If no pusher element is used, it can be planned to get the cutting element detached from the male part subsequently to the collecting operation and close the tube, or to provide for an additional plug for the tube of the storage device. A simple tube without tube head and without weighting element, possibly closed by a lid, can also be used according to different embodiments of the invention.

According to yet other embodiments, the male part can have a shape different from the one illustrated in FIGS. 2 to 5. In particular, the male pin 31 and its head 32 can have an appreciably identical diameter. In this way, it is possible to ensure a clean cutting of the ear in limiting risks of tearing. According to other embodiments, it is also possible to use a biopsy needle sliding within the male pin rather than a punch fixed to the end of the male pin.

The invention thus makes it possible to carry out optimized tagging and collecting operations simply and speedily for the user who does not himself have to perform several actions to perforate the animal's tissue, push the sample into the storage device, close the storage device, close the head of the female part, etc, since all these operations that can advantageously be done by means of a single action on the positioning tool (for example a manual, electrical, pneumatic or other action on the handles of the tool).

The invention claimed is:

1. A system for identifying an animal comprising:
an identification tag configured to be placed and to stay on the animal, comprising:
a male part, comprising a male pin cooperating with at least one cutting element intended to cut out a sample of animal tissue,
a female part configured to receive at least partially the male pin of the male part, the female part having an open head having a through-channel comprising a first end facing the male part when the male and female parts are fit together, and a second end opposite to the first end, and
at least one identifier selected from the group consisting of a visual identifier and an electronic identifier for identifying the animal; and
a detachable storage device for storing said sample, intended to be fixed to the second end of said through-channel;
wherein said system also comprises means for closing said head of the female part configured to take at least two positions, including an open position prior to a collecting, in which said through-channel is open and said detachable storage device is fixed to the second end of said through-channel, enabling a passage of said sample through the through-channel, and an irreversible closed position after the collecting, in which said through-channel is closed at said second end and said detachable storage device is detached from the second end of said through-channel; and
wherein said system also comprises means for preventing a return of said head of the female part to said open position from said irreversible closed position.

2. The system for identifying an animal according to claim 1, wherein:
said means for closing comprise at least one shutter that is mobile between said open and closed positions,
said at least one shutter is held in position by said storage device in said open position, and
said at least one shutter shuts off said through-channel at said second end in said closed position.

3. The system for identifying according to claim 2, wherein said at least one shutter comprises two shutters, called jaws, such that, in said open position, said jaws are stressed in opening and hold said storage device and, in said closed position, said jaws are released and shut off the through-channel at said second end.

4. The system for identifying an animal according to claim 1, wherein said system comprises a reinforcement element inserted into the male pin of said male part intended to reinforce rigidity of said male pin during the collecting.

5. The system for identifying an animal according to claim 1, wherein said male part, said female part and said storage device each carry at least one of said at least one identifier, enabling said animal to be identified.

6. The system for identifying an animal according to claim 1, wherein said system for identifying also comprises a pusher element that is mobile relative to said cutting element, enabling said sample to be pushed into said storage device and enabling said storage device to be shut off.

7. A system for identifying an animal comprising:
an identification tag configured to be placed and to stay on the animal, comprising:
  a male part, comprising a male pin cooperating with at least one cutting element intended to cut out a sample of animal tissue,
  a female part configured to receive at least partially the male pin of the male part, the female part having an open head having a through-channel comprising a first end facing the male part when the male and female parts are fit together, and a second end opposite to the first end, and
at least one identifier selected from the group consisting of a visual identifier and an electronic identifier for identifying the animal; and
a detachable storage device for storing said sample, intended to be fixed to the second end of said through-channel;
wherein said system also comprises means for closing said head of the female part configured to take at least two positions, including an open position prior to a collecting, in which said through-channel is open and said detachable storage device is fixed to the second end of said through-channel, enabling a passage of said sample through the through-channel, and an irreversible closed position after the collecting, in which said through-channel is closed at said second end and said detachable storage device is detached from the second end of said through-channel;
wherein said means for closing comprise a spring-forming part comprising at least two mobile jaws, such that, in said open position, said jaws are stressed in opening and hold said storage device and, in said closed position, said jaws are released and shut off the channel at said second end, and wherein said jaws comprise tabs preventing a return of the jaws from the irreversible closed position to the open position.

8. The system according to claim 7, wherein said means for closing also comprise a plug, and wherein, in said closed position, said jaws shut off the channel in a vicinity of said second end of said through-channel by locking said plug.

* * * * *